United States Patent [19]

Welkowitz et al.

[11] Patent Number: 4,993,420
[45] Date of Patent: Feb. 19, 1991

[54] METHOD AND APPARATUS FOR NONINVASIVE MONITORING DYNAMIC CARDIAC PERFORMANCE

[75] Inventors: Walter Welkowitz, Metuchen; Oing Cui, Highland Park; Yun Qi, Piscataway, all of N.J.

[73] Assignee: Rutgers University, Piscataway, N.J.

[21] Appl. No.: 502,409

[22] Filed: Mar. 30, 1990

[51] Int. Cl.⁵ ............................................... A61B 5/02
[52] U.S. Cl. ................................. 128/668; 364/413.05; 128/691
[58] Field of Search ........... 128/668, 687, 691, 661.08, 128/702; 364/413.02, 413.03, 413.04, 413.05, 413.06

[56] References Cited

U.S. PATENT DOCUMENTS

| | | | |
|---|---|---|---|
| 3,759,247 | 9/1973 | Doll et al. | 128/691 |
| 4,425,922 | 1/1984 | Conti et al. | 128/696 |
| 4,742,458 | 5/1988 | Nathans et al. | 128/702 |
| 4,889,132 | 12/1989 | Hutcheson et al. | 128/680 |

*Primary Examiner*—Francis Jaworski
*Assistant Examiner*—George Manuel
*Attorney, Agent, or Firm*—Lackenbach Siegel Marzullo & Aronson

[57] ABSTRACT

A method and apparatus for monitoring the cardiac output of living subjects. Carotid pulse waveforms and femoral pulse waveforms are measured and converted to digitized signals. The carotid pulse signal or waveform is applied as a voltage to the simulated aorta circuit and the circuit component values varied to develop a waveform output best matching the femoral pulse electrical waveform.

18 Claims, 9 Drawing Sheets

METHOD AND APPARATUS FOR NONINVASIVE MONITORING DYNAMIC CARDIAC PERFORMANCE

BACKGROUND OF THE INVENTION

This invention relates to methods and apparatus for noninvasively, continuously and discretely monitoring dynamic cardiac performance of a living subject.

Cardiac output is an important parameter of the entire circulatory system since it determines the blood flow, and thereby, the transport of oxygen and nutrients, to all tissues of the body. Heart disease can result in a decrease of cardiac output leading to inadequate nutrition of the cells of the body. Therefore, measuring cardiac output is useful in monitoring the critical ill patient, in rehabilitation medicine, and in medical screening.

Cardiac output may be expressed as the product of heart rate and volume of blood pumped per beat of the heart. Thus, under conditions of a consistent heart rate and stroke volume;

Cardiac Output = (Heart Rate) (Stroke Volume)

$$\frac{Liters}{Min} = \frac{Beats}{Min} \times \frac{Liters}{Beat}$$

Cardiac output or blood flow is also directly proportional to mean blood pressure and inversely proportional to peripheral resistance of the artery through which the blood flows (i.e. the aorta).

Because of the importance of changes in cardiac output and the difficulties in its direct measurement, the estimation of cardiac output and stroke volume from blood pressure pulse waveforms has been extensively studied. McDonald (1974) recorded two pressure pulses 3–5 cm apart in the ascending aorta. Both pulses were subjected to Fourier analysis and the apparent phase velocity was calculated for each harmonic of the pulses. The phase velocities were applied to the Wormsley equation to calculate aortic flow and stroke volume (the integral of aortic flow throughout one cycle). A problem encountered with this method is that the aorta exhibits non-uniform geometric elastic properties. To overcome the problem, Muthukrishnan and Jaron (1975) used a parameter optimization technique to compute aortic input impedance in a manner similar to Strano, Welkowitz and Fich (1972) based upon an aorta model developed by Welkowitz and Fich (1967). Instantaneous aorta flow waveforms were then calculated from the input impedance and the proximal aortic pressure. The aortic flow waveform estimated by this analysis closely matched the waveform measured using an electromagnetic flow meter. This method, however, which is based upon two pressure measurements, requires an invasive stroke volume estimation.

It is known that the hemodynamic characteristics of the aorta can be simulated by an R-L-C linear electrical network. Researchers have developed various aorta simulation models to perform estimations and calculations for different purposes. Based upon an equivalent electrical circuit model developed by Watts (1974) the aortic flow waveform can be calculated from the carotid input pulse waveform. A corresponding cardiac output then may also be computed. A microcomputer can be used for this simulation and calculation. The knowledge that the aorta can be represented by an electrical circuit model has led some researchers to seek a non-invasive method and apparatus for cardiac output monitoring using this circuit simulation.

SUMMARY OF THE INVENTION

In a method according to the present invention, the aorta is simulated by an equivalent lumped parameter electrical circuit. This circuit is simulated in a computer using a commercial circuit simulation program. Simultaneous pulse contour waveforms are measured on the outside of the body of a patient above the carotid artery and the femoral artery. The carotid pulse waveform is converted to a voltage which is applied to the equivalent circuit as the input. The circuit output voltage waveform and the femoral pulse waveform are compared on the computer screen. The equivalent circuit parameters are then adjusted by means of the computer keyboard until the "best" match of these two waveforms is obtained (e.g. by visual inspection). The input current to the circuit is then determined since that current is the analog of the aortic flow and it too is displayed on the computer screen. Since the pulse measurements are not calibrated in pressure units, a conventional external systolic/diastolic arm cuff measurement of the subject can be used to calibrate the carotid pulse waveform input. The femoral waveform calibration is obtained from that of the carotid pulses waveform.

Specifically in a method according to the invention, the carotid pulse is sensed and converted to a carotid pulse electrical waveform and, simultaneously, the femoral pulse is sensed and converted to a femoral pulse electrical waveform. Both electrical waveforms are digitized. The digitized carotid pulse electrical waveform is applied as an electrical voltage input to the simulated aorta electrical circuit comprising lumped electrical parameters representing the various physiological parameters. An output electrical voltage waveform of the simulated circuit simulating the femoral pulse and the measured or sensed femoral pulse electrical waveforms are displayed. The simulated circuit parameters are adjusted until the best match of the two electrical waveforms is obtained (e.g. by visual inspection and comparison). The simulated circuit is then considered to be a representative model of the aorta of the living subject and an input current waveform corresponding to the aortic flow is calculated from the model.

The system according to the invention makes use of two piezoelectric pulse transducers, each with a conditioning filter and amplifier circuit and used to measure the carotid and femoral pulses. The electrical pressure signals developed are applied to a computer through an A/D converter or alternatively, to a multichannel cassette recorder.

As indicated, it is possible to bypass the cassette recorder by connecting the transducers directly to an A/D converter circuit board. In this way, the digitized signals are simultaneously loaded to a computer for analysis. However, if the recorder is used, the system provides outputs applied to the A/D converter which is a device compatible with the computer used. A sampling frequency is set to 50Hz by an associated computer program, and the number of sample points can be, for example, 100 for each channel. The sampling operation takes about two seconds and at least one complete pulse signal is obtained even if the patient's heart rate is as low as 30 beats per minute.

The output of the converter is applied to a microcomputer which can be in essence a so-called "software oscilloscope". An enhanced graphic monitor with color or monochrome is used to display the curves. Graphics boards are installed to drive the monitor and the A/D converter is also put inside the computer. A programmable printer is used to provide both text and graphic function hard copy. The waveforms on the screen can be "copied" to the printer paper just like those drawn on an expensive plotter.

Computer programs are provided which are written in BASIC as well as a circuit simulator. The programs are designed taking into account that the operators, such as physicians or clinicians who may not be fully familiar with computers. User friendly instructions are given step by step so that the operator can manage all the operations and obtain the experimental reports.

BRIEF DESCRIPTION OF THE DRAWINGS

The methods and apparatus for cardiac output monitoring according to the invention will be better understood from the following description, claims and appended drawings in which:

FIG. 3, 3A and 3B are diagramatic block diagrams of two embodiments of the apparatus of the invention.

DESCRIPTION OF THE PREFERRED EMBODIMENT

Figure 1:
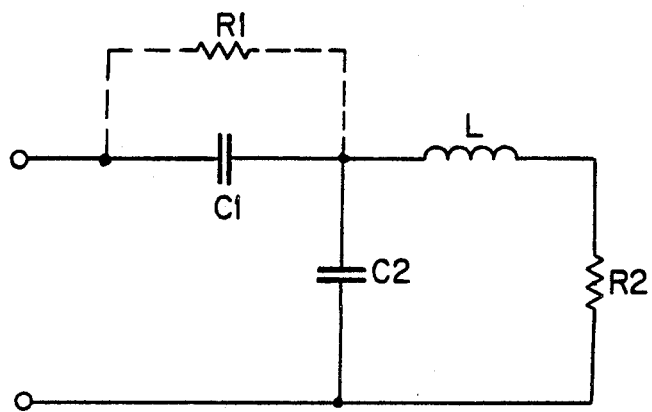
FIG. 1 is a circuit diagram of a basic electrical simulation circuit or model of an aorta.
Figure 3A:
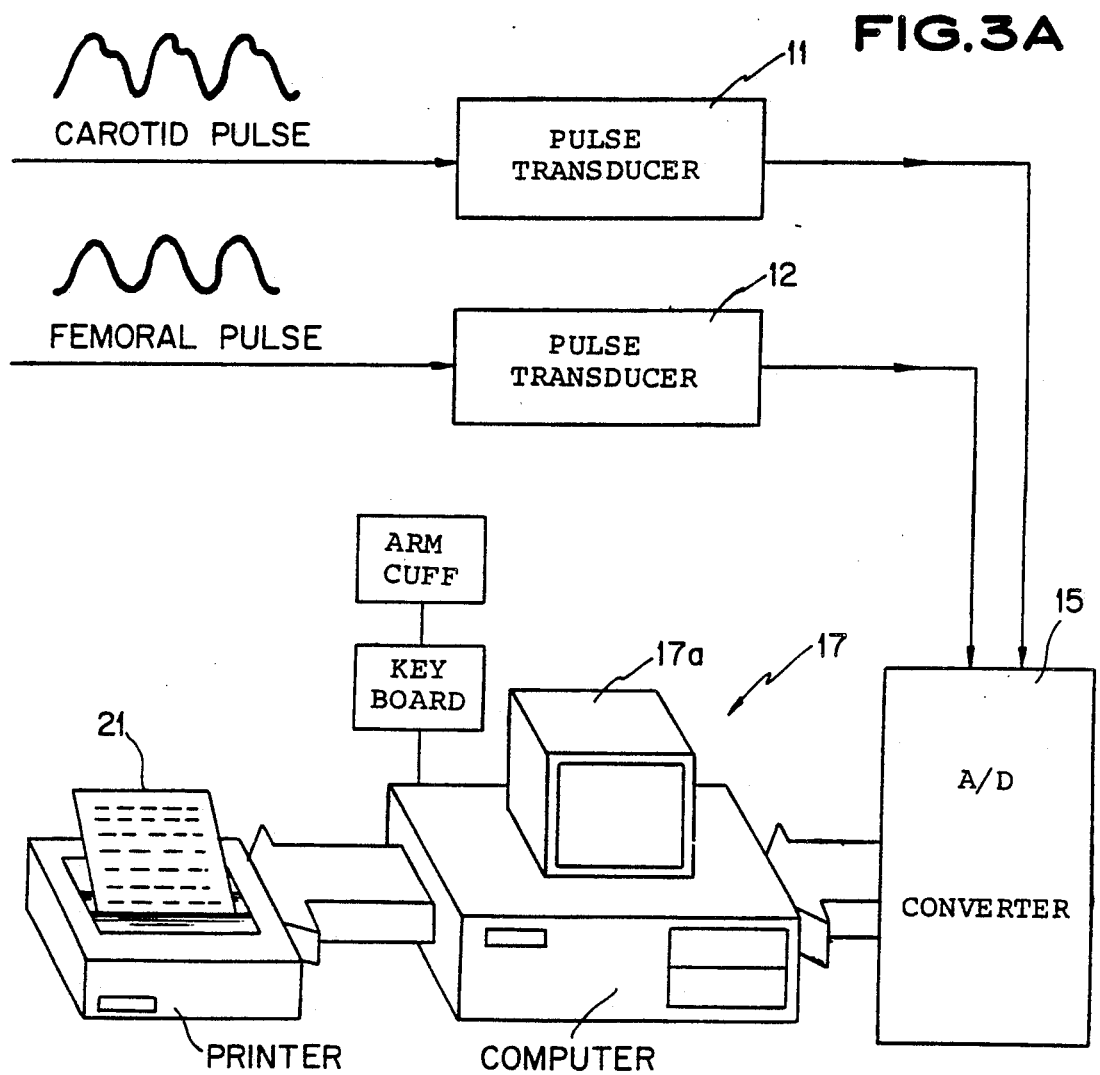

The system for carrying out the method according to the invention comprises, as shown in FIG. 3A, two pulse transducers 11, 12 which apply their outputs to an A/D converter 15. The outputs of the transducers 11, 12 are then digitized in the A/D converter 15 which applies the digitized analog signals to a computer 17, and a graphic printer 21 coupled to the computer prints out the text and graphics as required.

Figure 2:
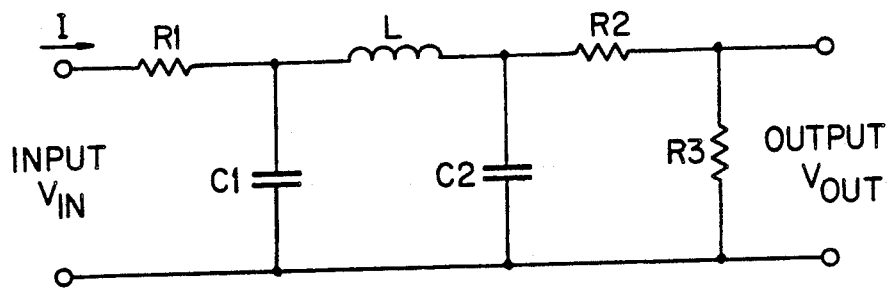
FIG. 2 is the simulated aorta circuit presently being used.

The aorta can be simulated by an electrical network as illustrated in FIG. 2. If $V_{in}$ is the waveform of the carotid pulse, it is possible to obtain a signal output $V_{out}$ which represents the femoral pulse. The current I then represents the aortic flow. In a method according to the invention, by comparing $V_{out}$ with the measured femoral pulse signal, it is possible to adjust parameters of the circuit to accurately represent the aorta. In this invention, the two piezoelectric pulse transducers 11, 12 are coupled to a conditioning filter and amplifier circuits, not shown, to sense the carotid and femoral pulses. The system provides a possible qualitative analysis of the readings. The pulse signals are digitized in the converter 15 and applied to the computer 17. Thus, the computer 17 has all the information about the simulated electrical circuit and the input and output voltage signals. By using commercially available circuit simulating programs, such as PSPICE, described hereinafter, it is possible to compute $V_{out}$ and I within a few minutes.

By displaying and comparing both the sensed and the calculated femoral waveforms, it is possible to determine whether the parameters of the simulated circuit within the computer should be modified. Further, when the calculated femoral waveform is sufficiently similar to the sensed femoral waveform, it is then possible to calculate other useful information such as heart rate, stroke volume and cardiac output. This can be done on several sets of data to minimize any error. If the error analysis suggests that further changes need to be made in the parameters of the circuit, then an optimal program can be generated to perform the modifications automatically, and the final results would be printed out in a specified form or saved as a document on disks in the computer 17.

Preferably, two piezoelectric pulse transducers 11, 12 are applied to the patient directly over the carotid and femoral regions and these sensed pulses are simultaneously recorded. The carotid pulse is converted to a voltage, then applied as input voltage to the simulated circuit. An output voltage $V_{out}$ produced by the simulated aorta circuit is measured, recorded and, preferably, is displayed. The parameters of the circuit are adjusted until the electronically generated output voltage waveform of the circuit substantially matches the sensed femoral pulse waveform. The equivalent flow waveform may then be calculated from the input current I of the circuit. Current I may then be recorded and processed to yield equivalent cardiac output.

Figure 3B:
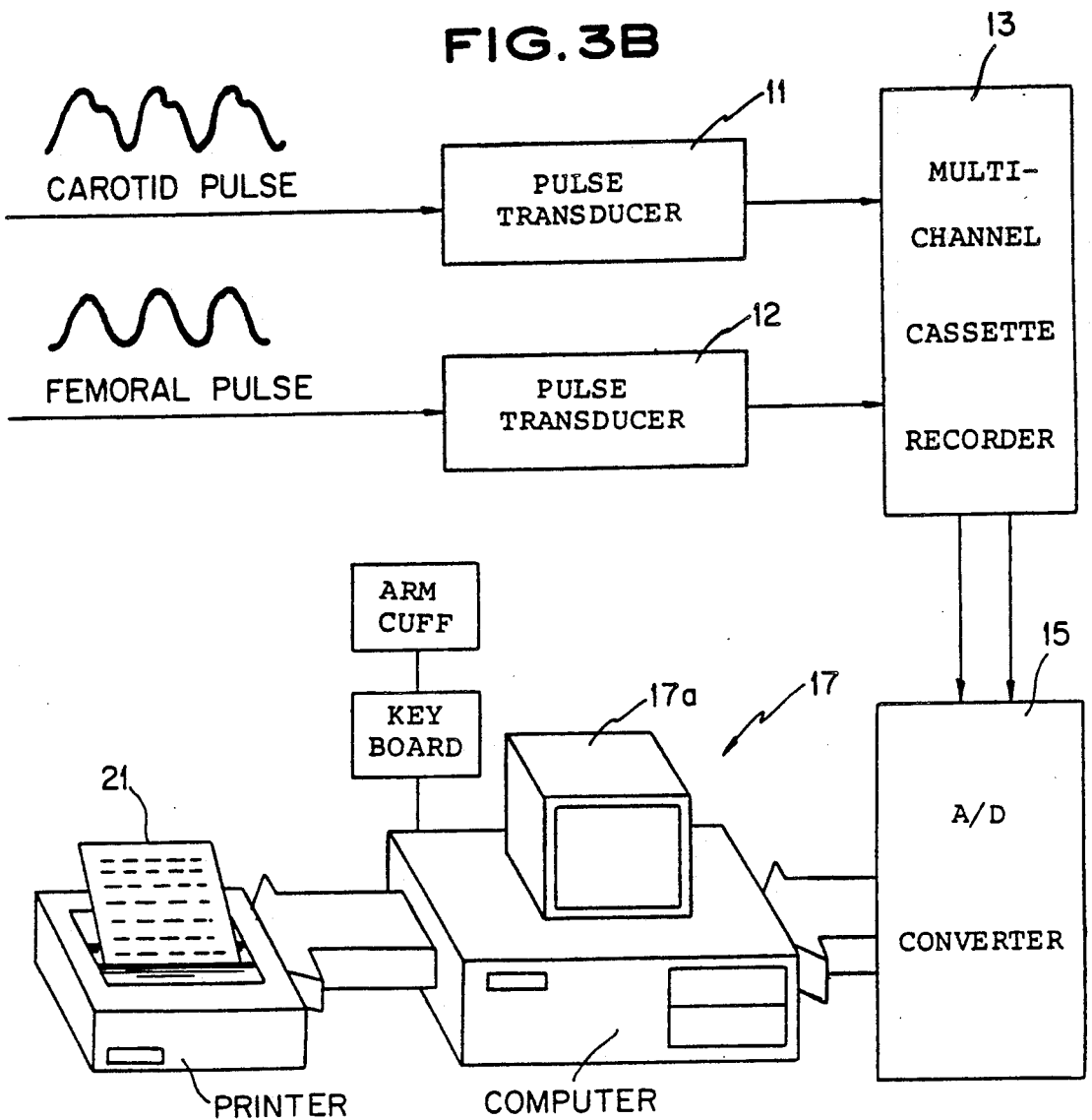

The system shown in FIG. 3B makes use of a channel cassette recorder 13 which is a memory for recording the outputs of the transducers 12 and the recorded signals are applied to the A/D converter. The system of the invention thus has two alternative embodiments. The programs disclosed are used with either embodiment.

The software in this system of the invention is made up of a group of programs or routines which are, for example, written in BASIC, along with a circuit simulating program, such as PSPICE produced by MicroSim Corporation. PSPICE is software which is capable of simulating an electrical circuit to determine DC, AC and transient responses for networks made up of resistors, inductors, capacitors, diodes, transistors, etc. For this invention, only determination of transient responses is necessary.

The overall software is designed to be "user friendly" for meeting the needs of operators, like physicians or clinicians, who may not be familiar with computers. Following instructions step by step, they can manage all the operations and obtain the experimental reports desired.

Figure 4:
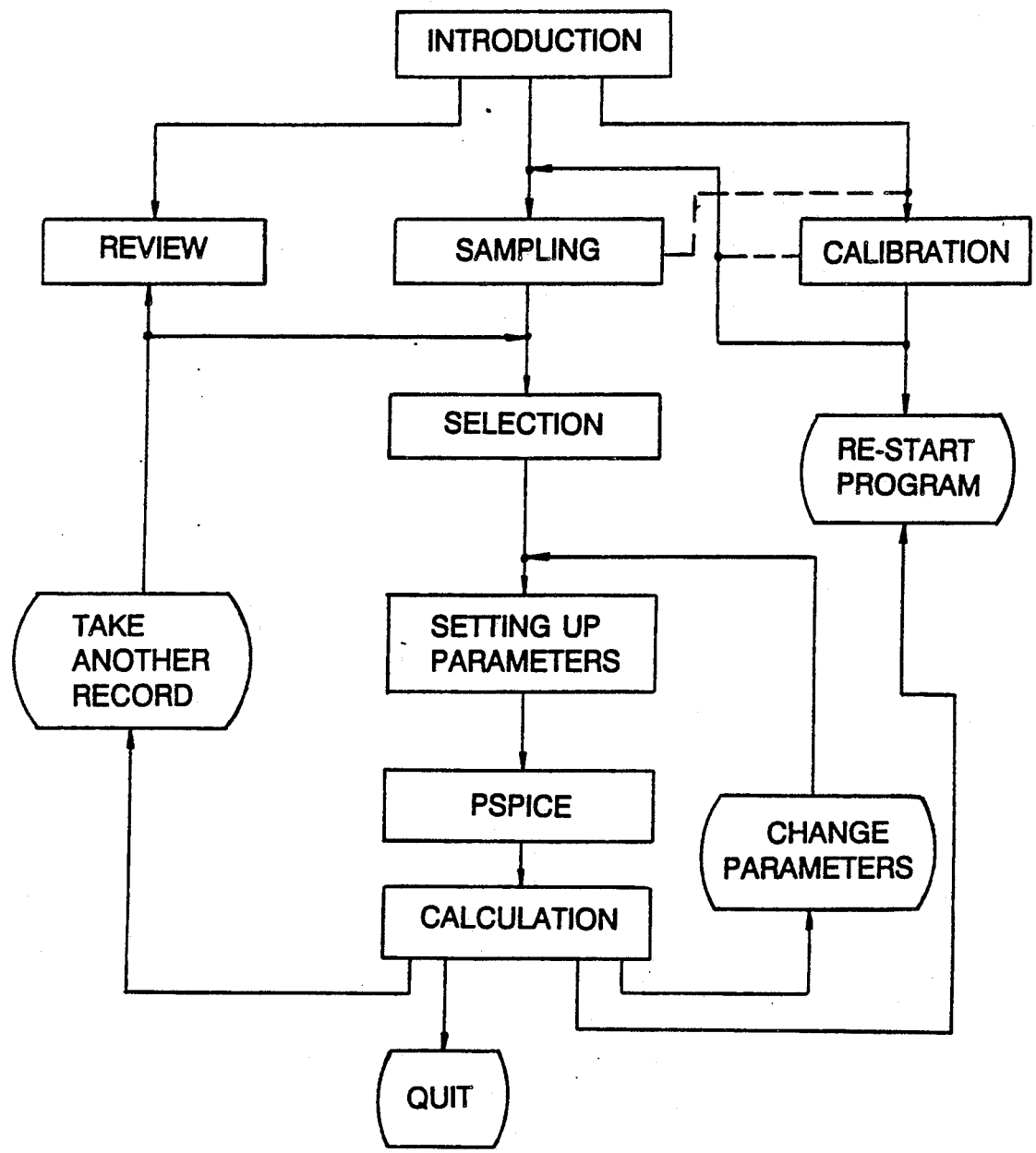
FIG. 4 is a block diagram of the whole system software, of which all the routines are shown in FIG. 4 through FIG. 10.

FIG. 4 is a flowchart of the overall system program. The function of each routine is discussed hereinafter with more details.

Figure 5:
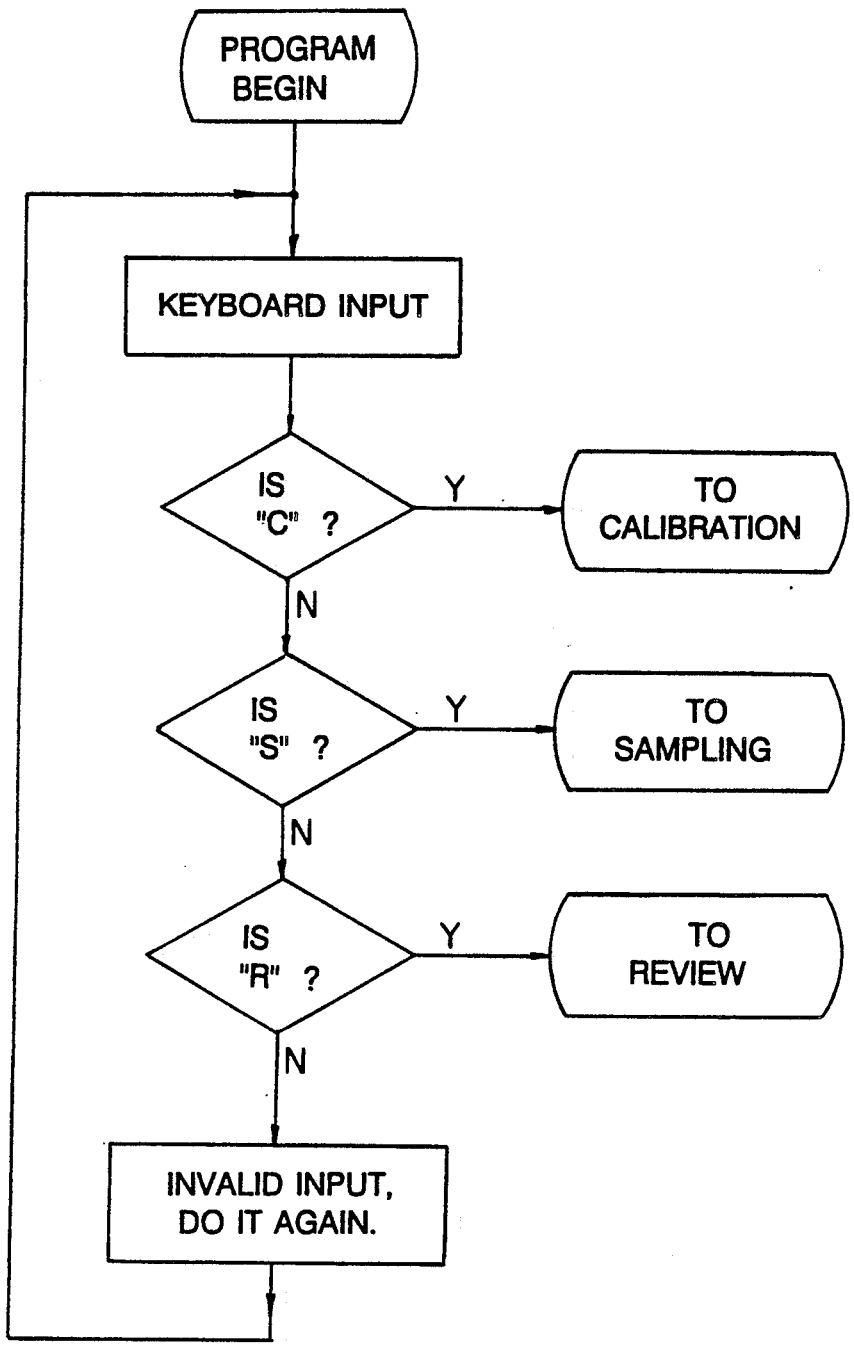
FIG. 5 is a flowchart of the INTRODUCTION routine of the software used in this invention.

The INTRODUCTION routine introduces a user to the system and allows for choosing between three routines. Specifically, as shown in the INTRODUCTION flowchart in FIG. 5, inputting the letter "C" allows a user to enter a CALIBRATION routine, inputting the letter "S" allows a user to enter a SAMPLING routine and inputting the letter "R" allows a user to enter a REVIEW routine. Inputting a character other than "C", "S", or "R" is considered unacceptable and the user would be prompted to enter an acceptable character.

The REVIEW routine allows reviewing of the records previously saved in memory. This routine allows the memory to be cleared so that all records can be newly created.

Figure 6:
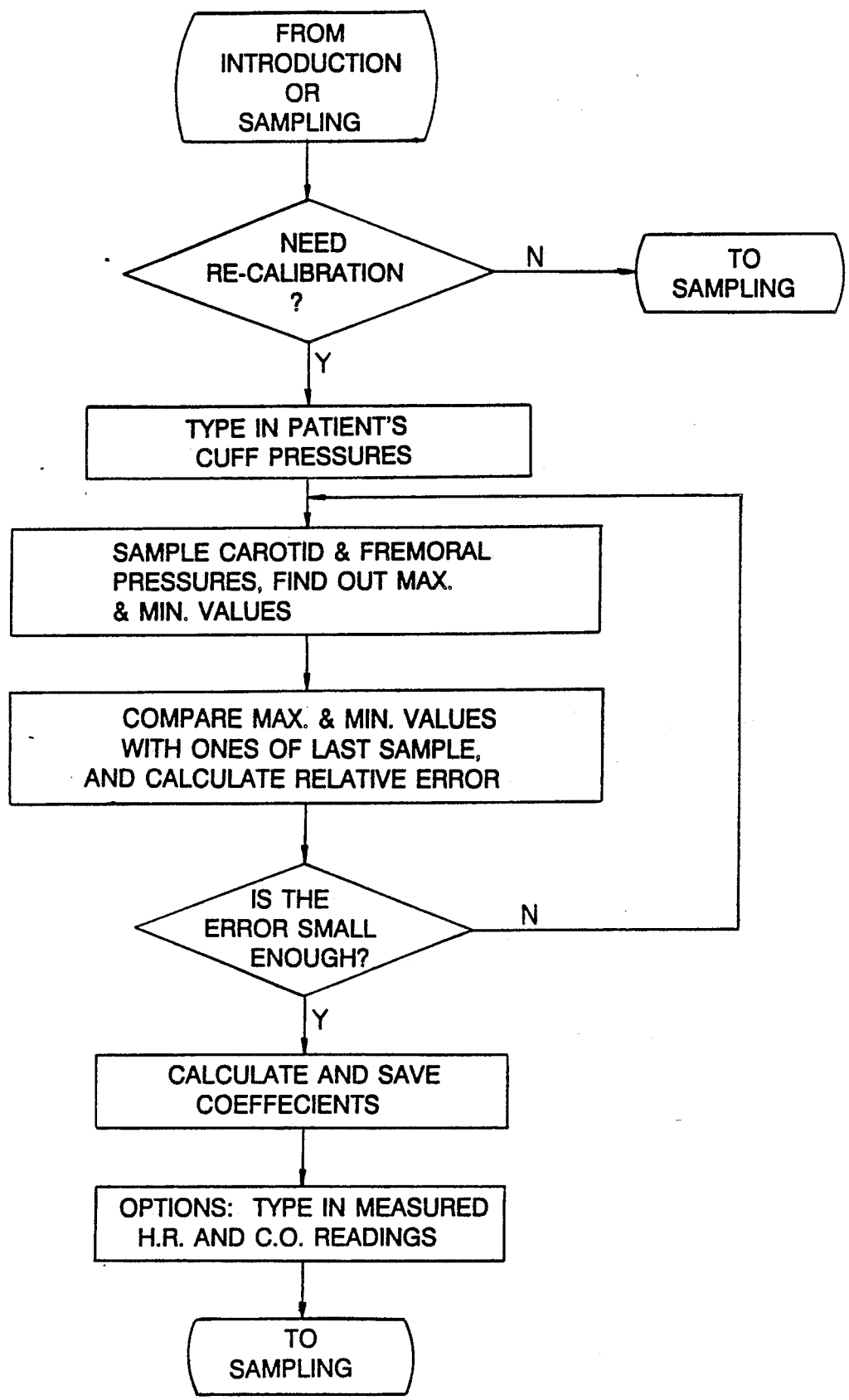
FIG. 6 is a flowchart of the routine of CALIBRATION in the software.
Figure 11:
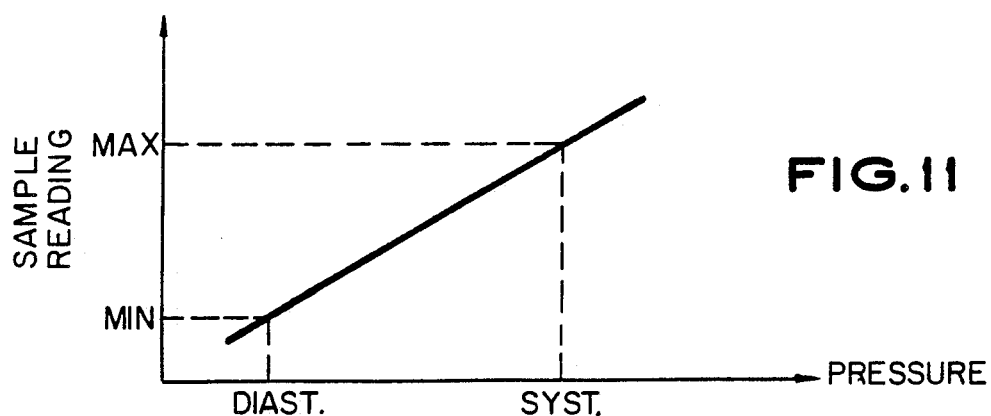
FIG. 11 is a diagram of the calibration.

The CALIBRATION routine allows a user to calibrate the carotid and femoral pulse input signals by changing coefficients associated with these signals. Specifically, coefficients are the slope and offset of a pressure-reading characteristic line associated with the sampled readings and cuff pressures, as shown in FIG. 11. Generally, calibration is only required to account for cuff pressure (Systolic and Diastolic readings) measured from a subject during the taking of data. FIG. 6 shows a flowchart for the CALIBRATION routine.

As shown in FIG. 6, at the beginning of the CALIBRATION routine, it is necessary to first determine whether or not calibration is required at all. The reason for this is because once the signals are calibrated, new calibration coefficients are calculated and these replace the original ones.

More particularly, as shown, the user must determine whether re-calibration is required. If the answer is no ("N"), then the CALIBRATION routine is exited, the SAMPLING routine is entered and, the current calibration remains unchanged. If the answer is yes ("Y"), then the carotid pulse signal is sampled and compared with results from a previous sample. When the error between them is small enough, such as 1%, new coefficients are calculated. Typically, the coefficients obtained are then saved in a file in which the original contents are replaced. Upon completion of the CALIBRATION routine, the SAMPLING routine is entered.

Figure 7:
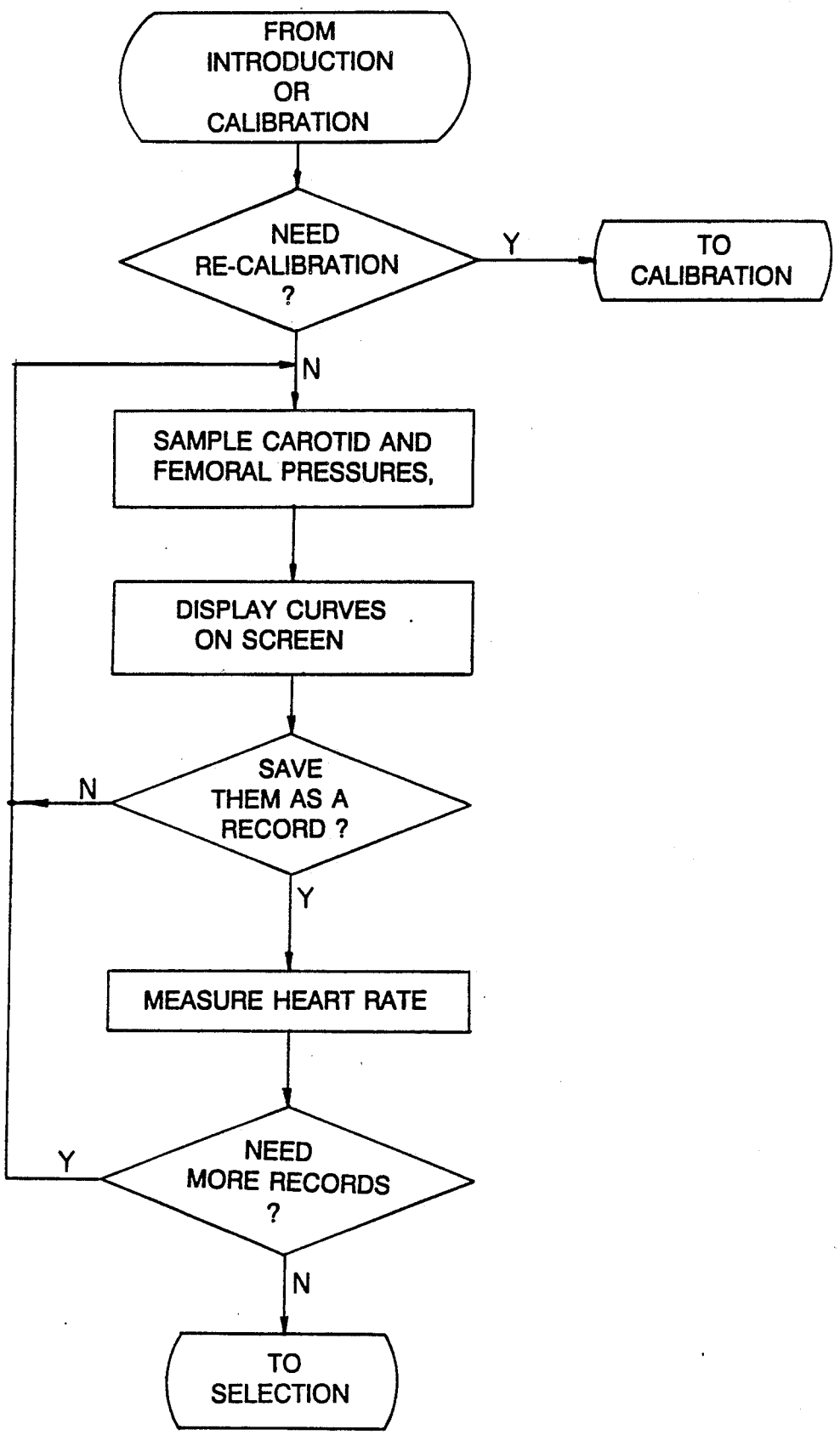
FIG. 7 is a flowchart of the SAMPLING routine of the software.

The SAMPLING routine allows a user to reject a sample or to save it in the memory so that only samples which are considered to be acceptable are saved. The flowchart of the SAMPLING routine is shown in FIG. 7. Similar to the CALIBRATION routine, a user is given the opportunity to re-calibrate the signals. If a user chooses to re-calibrate ("Y"), the user is returned to the CALIBRATION routine. If a user chooses not to re-calibrate ("N"), the original coefficients are maintained for the carotid pressure and femoral pressure samples which are then sampled through the A/D converter and displayed on the screen.

Upon displaying the sample on the screen, the user is asked whether or not to save the sample as a record. If the user chooses not to save the sample, it will be ignored and the sampling process will continue. If the user chooses to save the sample as a record, then the heart rate is measured from the curves displayed on the screen. Preferably, the operator manually makes adjustments to measure heart rate by, for example, moving two arrow-like cursors left and right on the screen using computer keys to cover an entire period of the heart beat to compute the heart rate. A proper or reasonable range of heart rate, for example, less than 200 and greater than 30, can be established in the program, so that data not within this range will not be taken into account.

When the SAMPLING routine is finished, records having files are saved in memory, for example, in the following format:

| | |
|---|---|
| CAR1.DAT | FEM1.DAT |
| CAR2.DAT | FEM2.DAT |
| CAR3.DAT | FEM3.DAT |
| . | . |
| . | . |
| . | . |

Note that each record includes a carotid data file and a femoral data file.

The SELECTION routine allows a user to select a set of input signals (a record) and to set up an input file for PSPICE.

Figure 8:
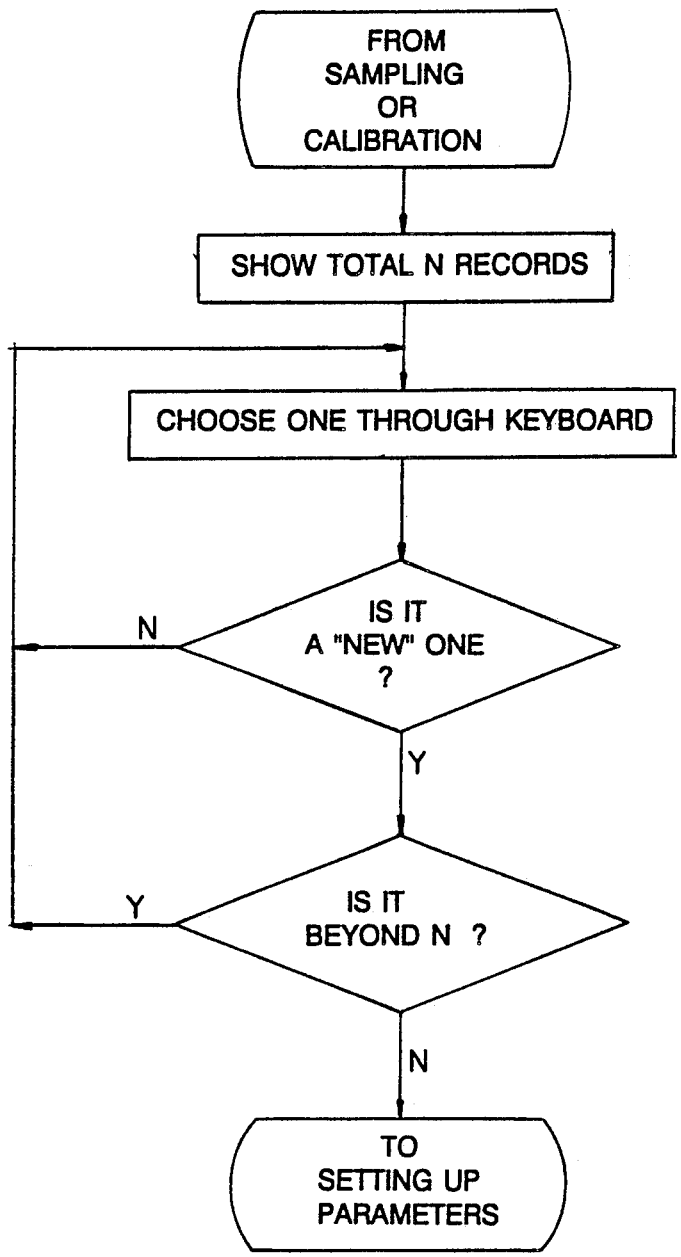
FIG. 8 is a flowchart of the SELECTION routine of the software.

The SELECTION routine flowchart is shown in FIG. 8. The record chosen must be a "new" one, that is, one which has not been treated before. This selected record is used in the next three software routines: SETTING UP PARAMETERS, PSPICE and CALCULATION, discussed hereinafter.

The equivalent circuit of the aorta, shown in FIG. 2, is based upon the aorta model developed by Welkowitz and Fich. The input signal applied to the circuit is the carotid pressure pulse waveform. By adjusting the values of R1, R2, R3, C1, C2 and L, it is possible to adjust the output signal $V_{out}$ of the circuit to match the measured femoral pressure pulse waveform. The input current I is then considered to be the represented aortic flow.

Figure 9:
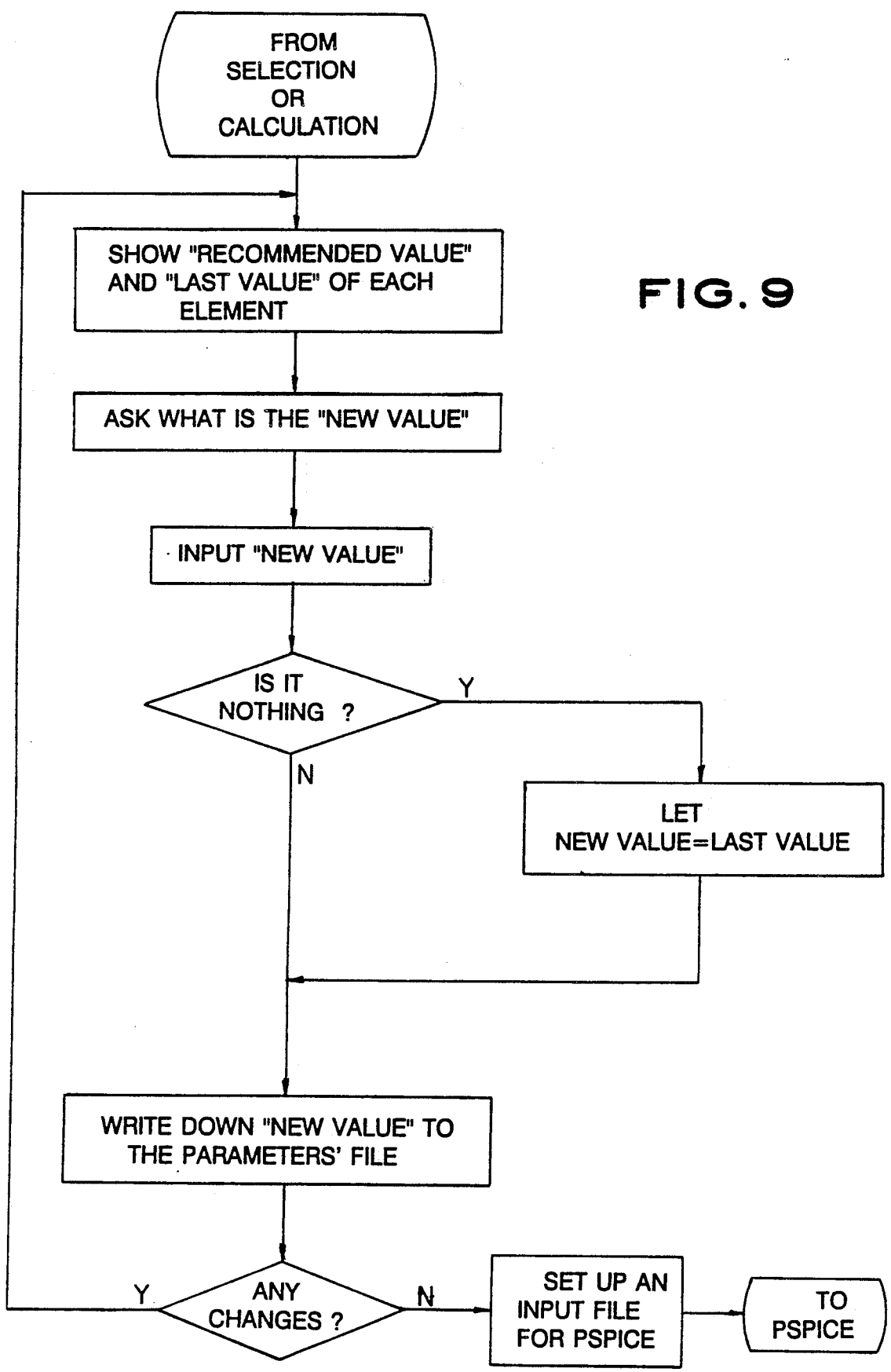
FIG. 9 is a flowchart of the PARAMETERS routine of the software.

The SETTING UP PARAMETERS routine flowchart is shown in FIG. 9. The "recommended" value referred to therein is an appropriate predicted number determined by previous experiments; it provides a good starting point or the simulation. The "last value" is the number adopted in the last case. If no "new value" is chosen, then the "new value" is made equal to the "last value" and saved in a parameters file. However, if a "new value" is chosen, it automatically replaces the "last value" in the parameters file. Using the new set of parameters in the parameters file, the SETTING UP PARAMETERS routine then sets up an input file for PSPICE. Conventionally, PSPICE is an electronic circuit simulator which requires an input file having all the information about the model circuit. As known by those skilled in the art, the input file for PSPICE actually is a list of instructions which specify the model circuit structure, including the type of input signal, where the input signals are applied, where the output signals are picked up, etc.

Using PSPICE to analyze the model circuit rather than a realized network physically built by electronic components is of great advantage to the system of the invention. Firstly, changing parameters or values of the components can be easily accomplished by keyboard input. As such, it is more convenient then physically changing electrical components in a circuit. Secondly, some electronic components may be too large to be conveniently connected in a circuit, such as a 30 H inductor, or an 100 uF non-polar capacitor. Moreover, in a real electrical circuit, for measuring current flowing through a branch, a small resistor is typically connected in that branch in series so as to pick up the voltage drop which represents the current. However, connecting such a resistor would change the property of the circuit. Thirdly, results obtained from PSPICE are already digitized and calibrated and not mere curves on a screen of an oscilloscope. Accordingly, these results can be utilized in calculations without further transformation.

Figure 10:
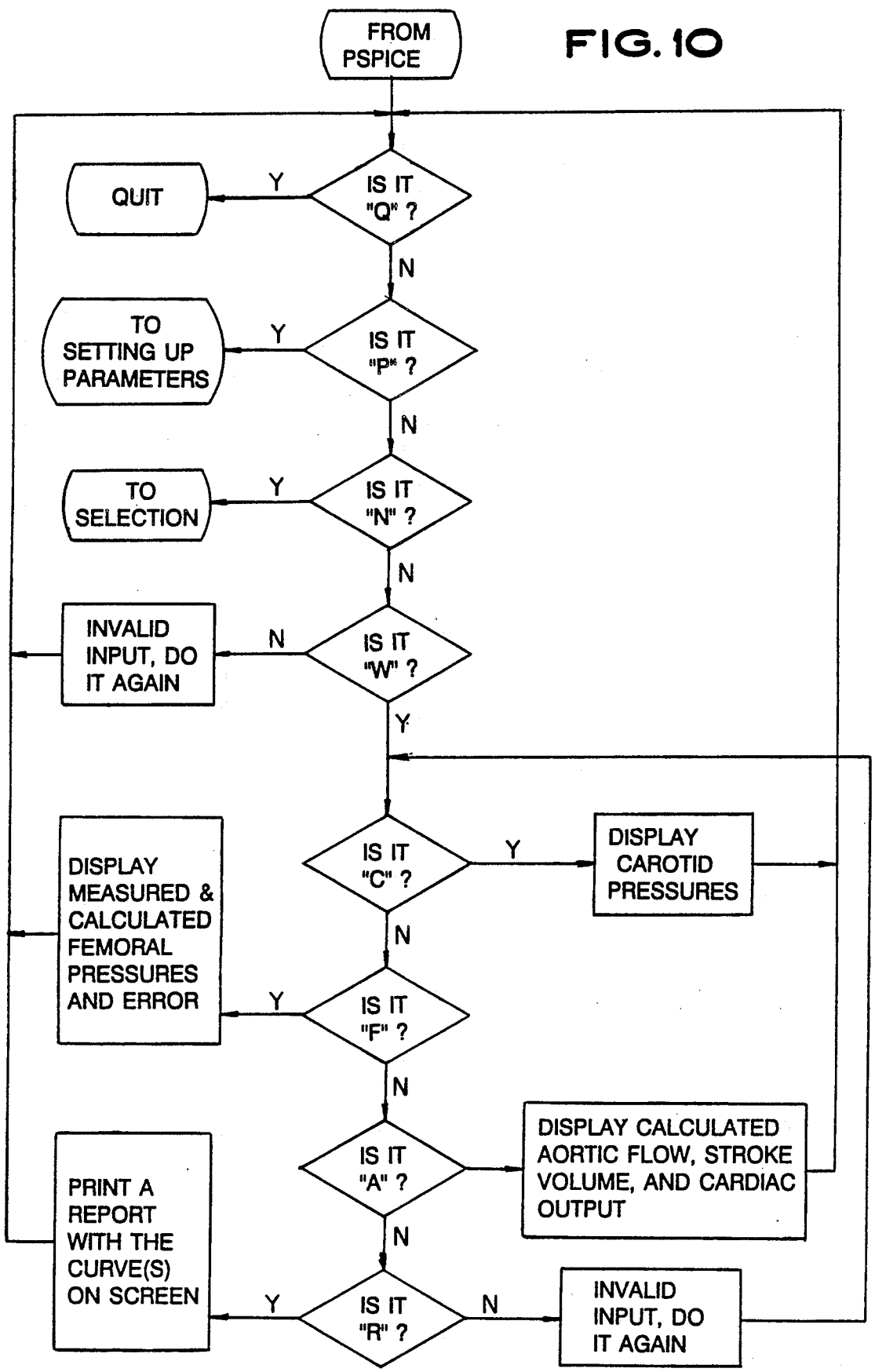
FIG. 10 is a flowchart of the CALCULATION routine of the software.

The CALCULATION routine flowchart is shown in FIG. 10. Once the CALCULATION routine is entered from PSPICE, a user has the following four options:

(1) Quit from the program ("Q"), and return to system DOS;

(2) Go back to the SETTING UP PARAMETERS ("P") routine to change values of components of the equivalent circuit;

(3) Go back to the SELECTION ("N") routine to pick up the Next record; and (4) Display the Waveforms on the screen ("W").

Following the "W" option, there are four additional options:

(1) Display the Carotid waveform ("C");

(2) Display both the measured and calculated Femoral pressure signals ("F"). If this option is chosen, simultaneous with displaying the signals, mean pressure for both signals and their relative error are computed as a reference for evaluation. Typically, relative error is determined by the following formula:

$$\text{error} = \frac{M.M.P - C.M.P}{M.M.P} \times 100\%$$

where,
M.M.P ---------- Measured Mean Pressure
C.M.P ---------- Calculated Mean Pressure (3) Display the Aortic flow signal calculated from the model circuit response ("A") which represents the calculated cardiac output.

(4) Print a Report (R). Experimental curves and all evaluations are printed out.

The method and apparatus disclosed provide a simple, fast and nonexpensive system for noninvasively determining or monitoring the cardiac output of the living subject being monitored.

While the invention is disclosed and more particularly described with the presently preferred embodiment, it is not intended that the invention be limited to the described embodiment. It will be recognized by those skilled in the art that modifications may be made without departing from the scope and spirit of the invention. Thus, it is intended that the appended claims cover all equivalent variations as may be subsequently contemplated.

What is claimed is:

1. Apparatus for noninvasively monitoring dynamic cardiac output and cardiovascular system parameters of a living subject comprising, means for sensing a carotid pulse waveform above the carotid artery externally on the body of the living subject and for converting the sensed pulse waveform to a carotid pressure electrical waveform and means for sensing a femoral pulse waveform above the femoral artery externally on the body of the living subject and for converting the sensed pulse waveform to a femoral pressure electrical waveform, means receptive of each electrical waveform for digitizing each electrical waveform individually, means for defining a simulated electrical circuit simulating an aorta in terms of lumped electrical parameters, means for applying the digitized carotid pressure electrical waveform as a simulated electrical voltage input to said simulated electrical circuit comprising lumped electrical parameters, means for driving the simulated electrical circuit receptive of the digitized carotid pressure electrical waveform and for variable adjustment of the electrical parameters thereof, means for comparing an output electrical waveform of the simulated circuit simulating the femoral pressure electrical waveform and the sensed femoral pressure electrical waveform, and means for adjusting individually the simulated circuit electrical parameters until corresponding instantaneous values of the last-mentioned two electrical waveforms match said simulated circuit electrical parameters.

2. Apparatus for noninvasively monitoring dynamic cardiac output and cardiovascular system parameters of a living subject according to claim 1, in which said means for sensing carotid pulse waveform and said means for sensing said femoral pulse waveform each comprise a piezoelectric pulse transducer for converting pulse waveform measurements to an electrical waveform.

3. Apparatus for noninvasively monitoring dynamic cardiac output and cardiovascular system parameters of a living subject according to claim 1, in which said means for digitizing comprises an A/D converter.

4. Apparatus for noninvasively monitoring dynamic cardiac output and cardiovascular system parameters of a living subject according to claim 1, in which said means for simulating said simulated electrical circuit comprises a computer.

5. Apparatus for noninvasively monitoring dynamic cardiac output and cardiovascular system parameters of a living subject according to claim 4, in which said means for variably adjusting the simulated electrical circuit comprises a keyboard for making manual inputs into the computer for adjusting the simulated circuit electrical parameters.

6. Apparatus for noninvasively monitoring dynamic cardiac output and cardiovascular system parameters of a living subject according to claim 4, further including means for displaying visually the electrical output waveform of the simulated electrical circuit and the femoral pressure electrical waveform comprising a monitor screen.

7. Apparatus for noninvasively monitoring dynamic cardiac output and cardiovascular system parameters of a living subject according to claim 1, in which each means for sensing pulse waveforms comprises a transducer.

8. Apparatus for noninvasively monitoring dynamic cardiac output and cardiovascular system parameters of a living subject according to claim 1, in which said means for simulating the simulated electrical circuit includes a simulator program, and further includes means for obtaining from the simulated circuit, an input electrical current waveform of the simulated circuit corresponding to the aortic flow of the living subject.

9. Apparatus for noninvasively monitoring dynamic cardiac output and cardiovascular system parameters of a living subject according to claim 1, further including memory means for receiving and recording the carotid pressure electrical waveform and the femoral pressure electrical waveform.

10. A noninvasive method of monitoring dynamic cardiac output and cardiovascular system parameters of a living subject comprising, sensing carotid pulse waveforms above the carotid artery externally on the body of the living subject and converting the sensed pulse waveforms to a carotid pressure electrical waveform and sensing the femoral pulse waveform above the femoral artery externally on the body of the living subject and converting the sensed pulse waveform to a femoral pressure electrical waveform, digitizing both pressure electrical waveforms, applying the digitized carotid pressure electrical waveform as an electrical voltage input to a simulated aorta lumped electrical circuit consisting of lumped electrical parameters representing the various physiological parameters, displaying visually an output electrical waveform of the simulated circuit and the sensed femoral pressure electrical waveform, adjusting the simulated circuit parameters until the two last-mentioned electrical waveforms are matched, whereby the simulated circuit is then a model of the aorta of the living subject, and developing from the model an input current waveform corresponding to aortic blood flow.

11. A noninvasive method of monitoring dynamic cardiac output and cardiovascular system parameters of a living subject according to claim 10, including storing the sensed pulse waveforms temporarily prior to digitizing thereof.

12. A noninvasive method of monitoring dynamic cardiac output and cardiovascular system parameters of a living subject according to claim 10, including obtaining the carotid pulse waveform and the femoral pulse waveform by sampling on the living subject.

13. A noninvasive method of monitoring dynamic cardiac output and cardiovascular system parameters of a living subject according to claim 10, including copying the waveforms visually displayed automatically on a recording medium.

14. A noninvasive method of monitoring dynamic cardiac output and cardiovascular system parameters of living subject according to claim 10, including simulating the simulated aorta lumped electrical circuit prior to applying the carotid pressure electrical waveform as an electrical input thereto.

15. A noninvasive method of monitoring dynamic cardiac output and cardiovascular system parameters of a living subject according to claim 10, including measuring the heart rate of the living subject from the waveforms displayed.

16. Apparatus for noninvasively monitoring dynamic cardiac output and cardiovascular system parameters of a living subject comprising, means for sensing carotid pulse waveform above the carotid artery externally on the body of the living subject and converting the sensed carotid pulse waveform to a carotid pressure electrical waveform, arm cuff measurement means for calibrating from pulse amplitude to pressure and means for sensing a femoral pulse waveform above the femoral artery externally on the body of the living subject and converting the sensed femoral pulse waveform to a femoral pressure electrical waveform, arm cuff measurement means for calibrating from pulse amplitude to pressure, means receptive of each electrical waveform for digitizing each electrical waveform individually, means for applying the digitized carotid pressure electrical waveform as a simulated electrical voltage input to a simulated aorta lumped parameter electrical circuit comprising lumped electric parameters representing various physiological parameters, means for defining the simulated electrical circuit, means for driving the simulated electrical circuit receptive of the digitized carotid pressure electrical waveform and for variable adjustment of the parameters thereof, means for displaying visually an output electrical waveform of the simulated circuit simulating the femoral pressure electrical waveform and the sensed femoral pressure electrical waveform, and means for adjusting the simulated circuit parameters until matching of the last-mentioned two electrical waveforms are obtained by visual inspection.

17. A noninvasive method of monitoring dynamic cardiac output and cardiovascular system parameters of a living subject comprising, sensing a carotid pulse waveform above the carotid artery externally on the body of the living subject and converting the sensed carotid pulse waveform to a carotid pressure electrical waveform using an arm cuff measurement for calibrating from pulse amplitude to pressure, and sensing the femoral pulse waveform above the femoral artery externally on the body of the living subject and converting the sensed femoral pulse waveform to a femoral pressure electrical waveform, again using an arm cuff measurement for calibrating from pulse amplitude to pressure, digitizing both pressure electrical waveforms, applying the digitized carotid pressure electrical waveform as a simulated electrical input to a simulated aorta lumped electrical circuit comprising lumped electrical parameters representing the various physiological parameters, displaying visually an output electrical waveform of the simulated circuit simulating the femoral pressure and the sensed femoral pressure electrical waveforms, adjusting the simulated circuit parameters until matching of the last-mentioned two electrical waveforms obtains by visual inspection and comparison, whereby the simulated circuit is then a model of the aorta of the living subject, and developing from the model an input current waveform corresponding to aortic flow.

18. Apparatus for noninvasively monitoring dynamic cardiac output and cardiovascular system parameters of a living subject comprising, means for sensing a carotid pulse waveform above the carotid artery externally on the body of the living subject and for converting the sensed carotid pulse waveform to a carotid pressure electrical waveform and means for sensing a femoral pulse waveform above the femoral artery externally on the body of the living subject and for converting the sensed femoral pulse waveform to a femoral pressure electrical waveform, means receptive of each electrical waveform for digitizing each electrical waveform individually, means for defining a simulated electrical circuit simulating an aorta in terms of lumped electrical parameters, means for applying the digitized carotid pressure electrical waveform as a simulated electrical voltage input to said simulated electrical circuit comprising lumped electrical parameters, means for driving the simulated electrical circuit receptive of the digitized carotid pressure electrical waveform and for variable adjustment of the electrical parameters thereof, means for comparing an output electrical waveform of the simulated circuit simulating the femoral pressure electrical waveform and the sensed femoral pressure electrical waveform, and means for adjusting the simulated circuit parameters until matching of the last-mentioned two electrical waveforms are obtained by visual inspection.

* * * * *